US00PP22502P2

(12) United States Plant Patent
Olesen

(10) Patent No.: US PP22,502 P2
(45) Date of Patent: Feb. 21, 2012

(54) FLORIBUNDA ROSE PLANT NAMED 'POULCAS031'

(50) Latin Name: ***Rosa* hybrid**
Varietal Denomination: Poulcas031

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 12/930,444

(22) Filed: Jan. 7, 2011

(51) Int. Cl.
*A01H 5/00* (2006.01)

(52) U.S. Cl. ..... Plt./149; Plt./148

(58) Field of Classification Search ..... Plt./148, Plt./149

See application file for complete search history.

*Primary Examiner* — Kent L Bell

(57) ABSTRACT

A new garden rose plant of the compact floribunda class which has abundant, pink flowers and attractive foliage. This new and distinct variety has shown to be uniform and stable in the resulting generations from asexual propagation.

5 Drawing Sheets

Botanical designation: *Rosa* hybrid.
Variety denomination: 'Poulcas031'.

SUMMARY OF THE INVENTION

The present invention constitutes a new and distinct variety of garden rose plant which originated from a controlled crossing between the female seed parent, an unnamed, non-commercial seedling, and the male pollen parent, also an unnamed, non-commercial seedling.

The two parents were crossed during the summer of 1997 and the resulting seeds were planted in a controlled environment in Fredensborg, Denmark. The new variety, named 'Poulcas031', originated as a single seedling from the stated cross.

The new variety may be distinguished from its female seed parent by the following combination of characteristics:

1. The seed parent has dark red flowers. 'Poulcas031' has pink flowers.
2. The seed parent has more flower petals than 'Poulcas031'.

The new variety may be distinguished from its male pollen parent by the following combination of characteristics:

1. The pollen parent has over 75 petals. 'Poulcas031' has 40 to 50 petals.
2. Flowers of the pollen parent have a general tonality of Red Group 49A, while flowers of 'Poulcas031' are Red-Purple Group N 57A.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas031' from all other varieties of which we are aware.

As part of the rose development program, Mogens N. Olesen germinated the seeds from the aforementioned hybridization during winter of 1997 and conducted evaluations on the resulting seedlings in a controlled environment in Fredensborg, Denmark. 'Poulcas031' was selected in the spring of 1998 by the inventor as a single plant from the progeny of the aforementioned hybridization.

Asexual reproduction of 'Poulcas031' by traditional budding and rooted cuttings was first done by Mogens N. Olesen in the nursery in Fredensborg, Denmark in July, 1998. This initial and other subsequent asexual propagations conducted in controlled environments have demonstrated that the characteristics of 'Poulcas031' are true to type and are transmitted from one generation to the next.

BRIEF DESCRIPTION OF THE DRAWING

The accompanying color illustrations show as true as is reasonably possible to obtain in color photographs of this type, the typical characteristics of the buds, flowers, leaves, and stems, of 'Poulcas031'. Specifically illustrated in the drawing are.

DETAILED DESCRIPTION OF THE VARIETY

Figure 1:
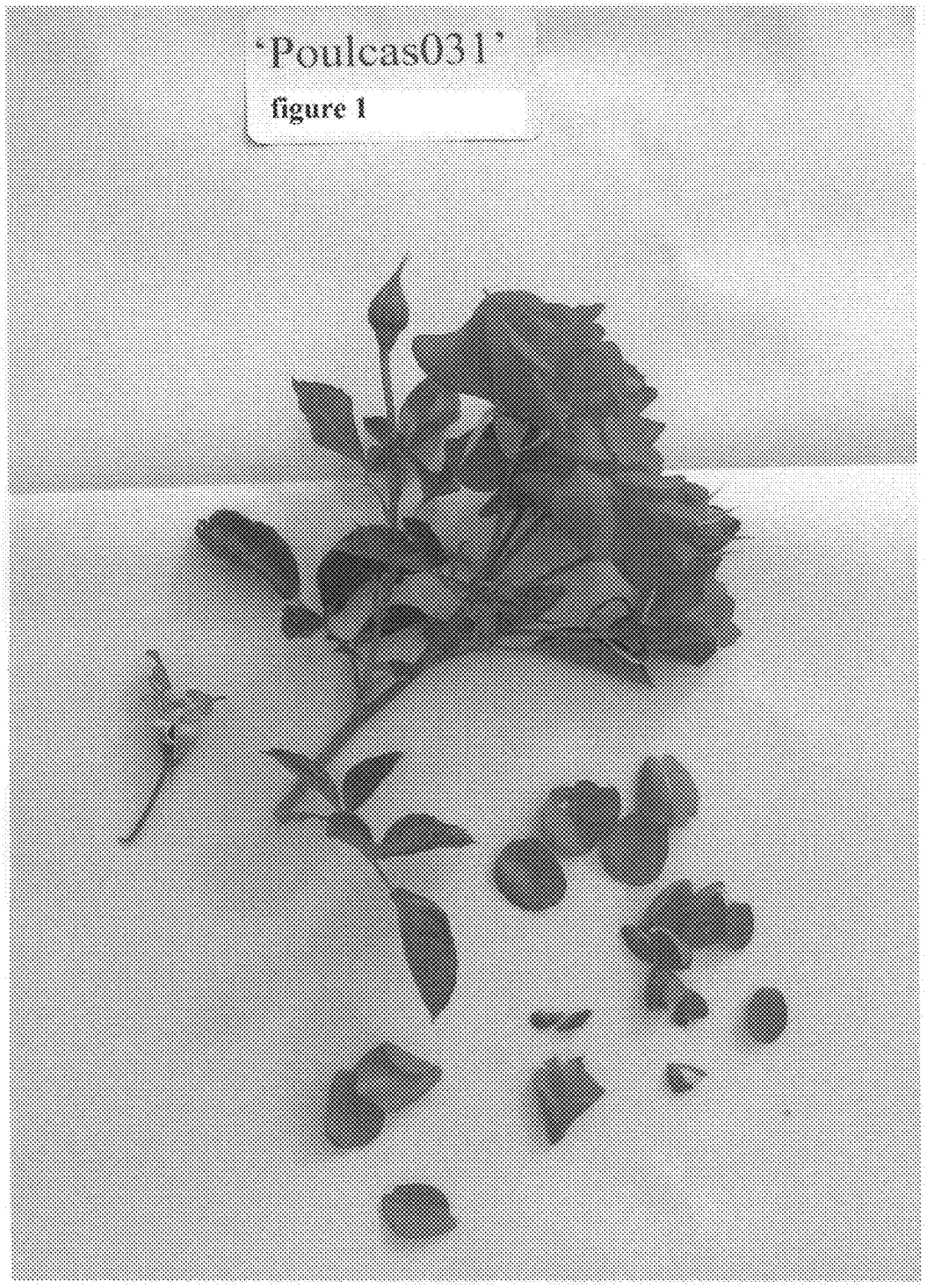
FIG. 1; Cluster of open flowers, showing flower bud, reproductive flower parts and detached petals.
Figure 2:
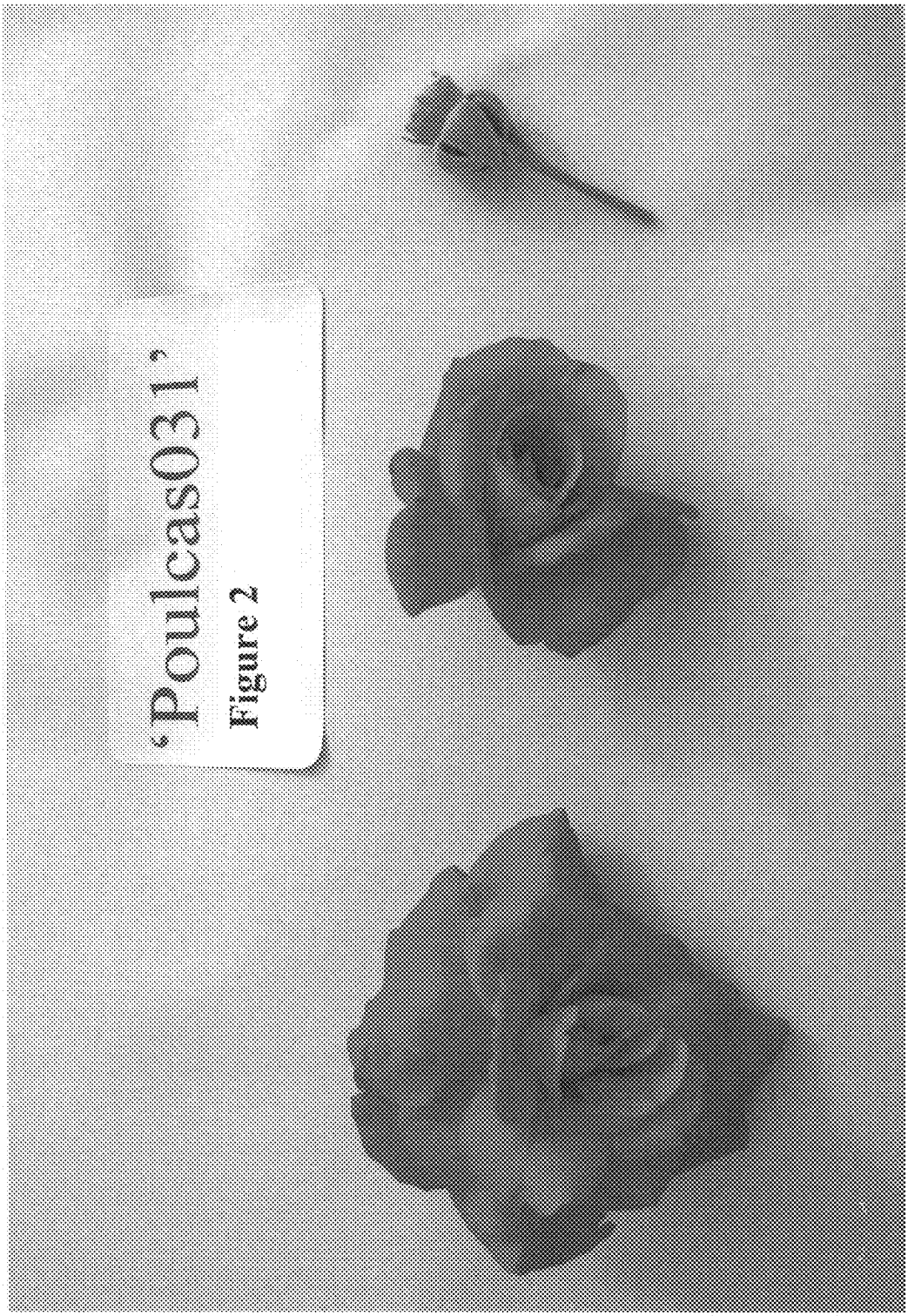
FIG. 2; Open flowers and reproductive flower parts.
Figure 3:
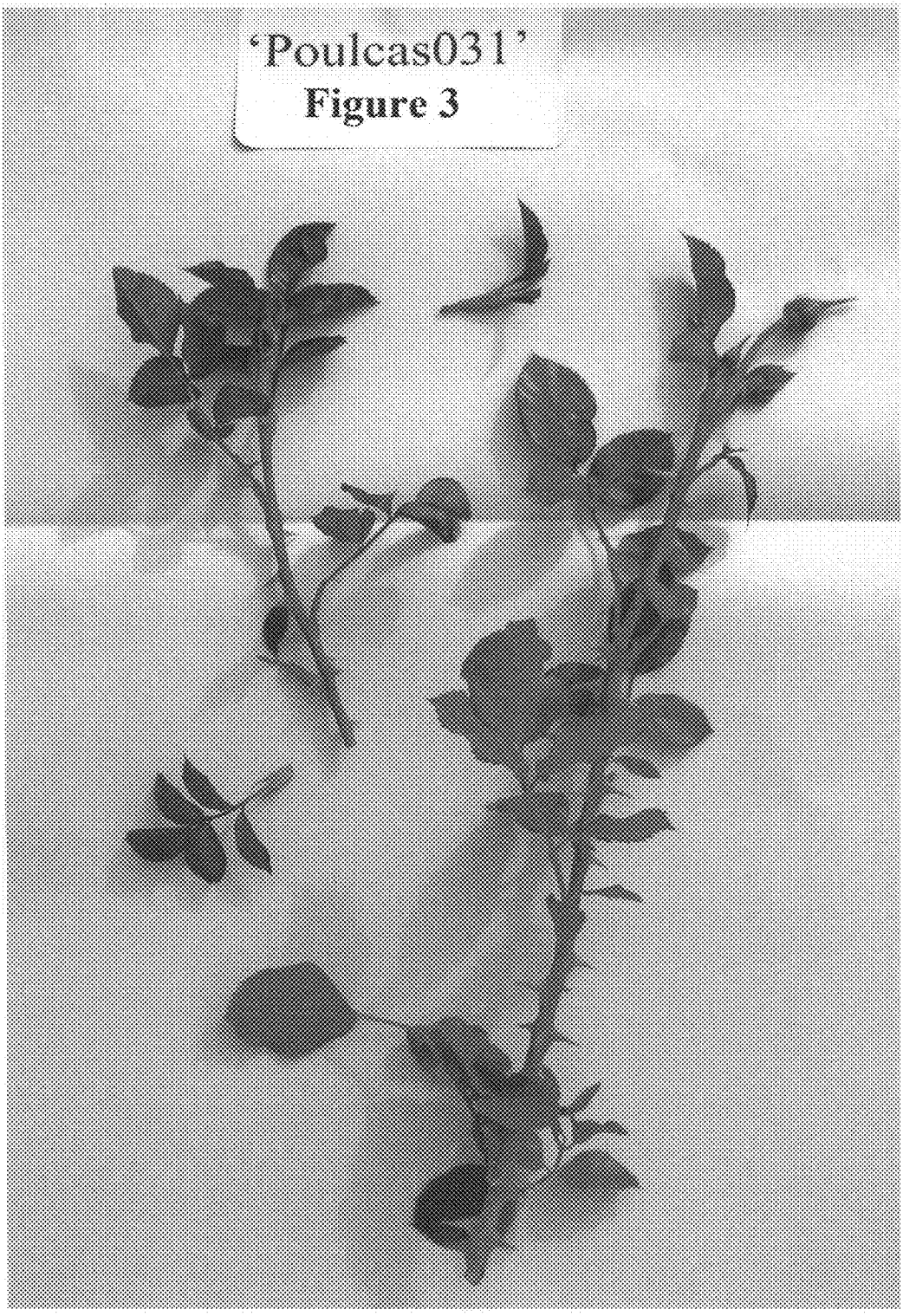
FIG. 3; Stems showing attachment of leaves, mature and juvenile growth.
Figure 4:
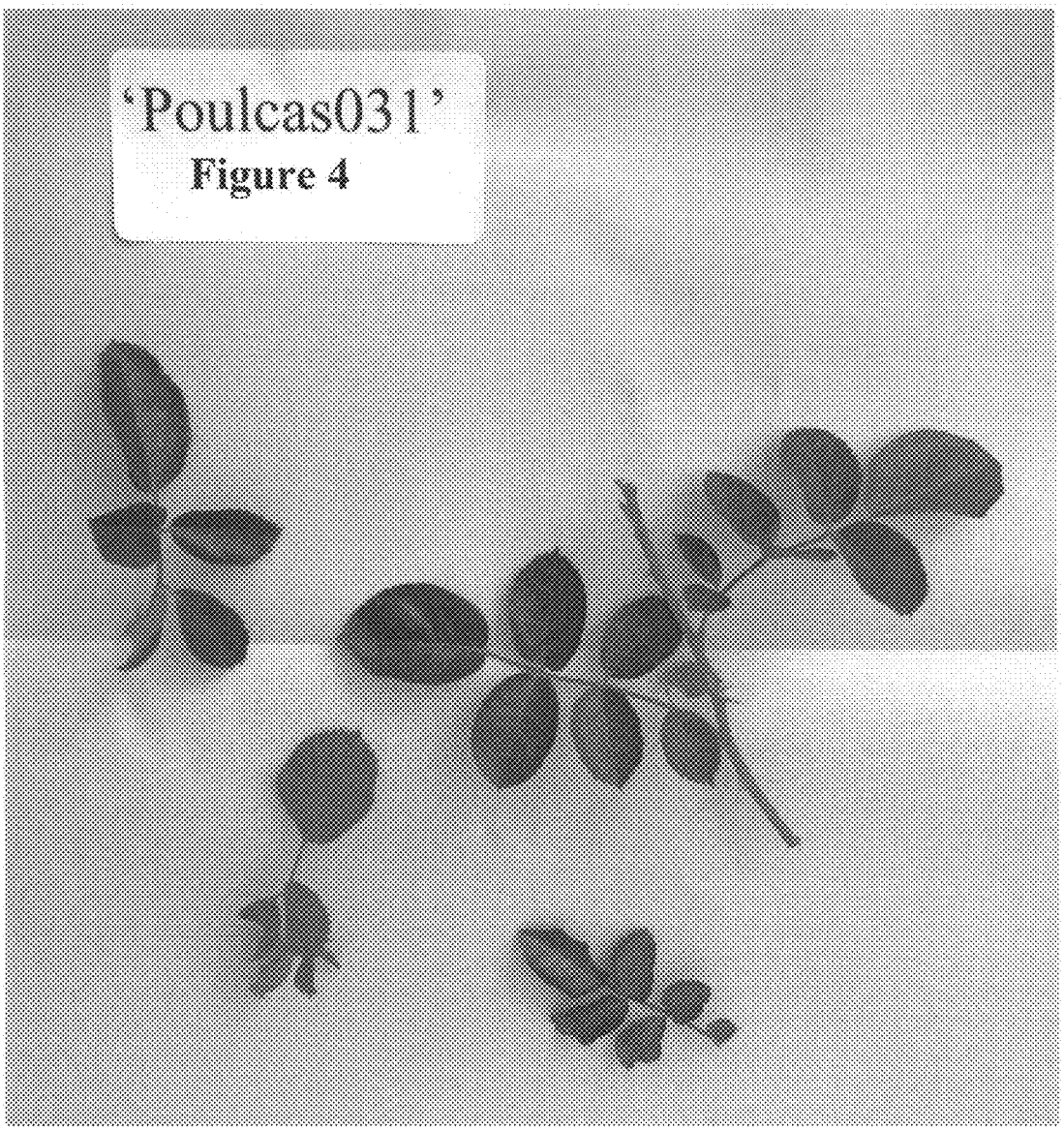
FIG. 4; Leaves.
Figure 5:
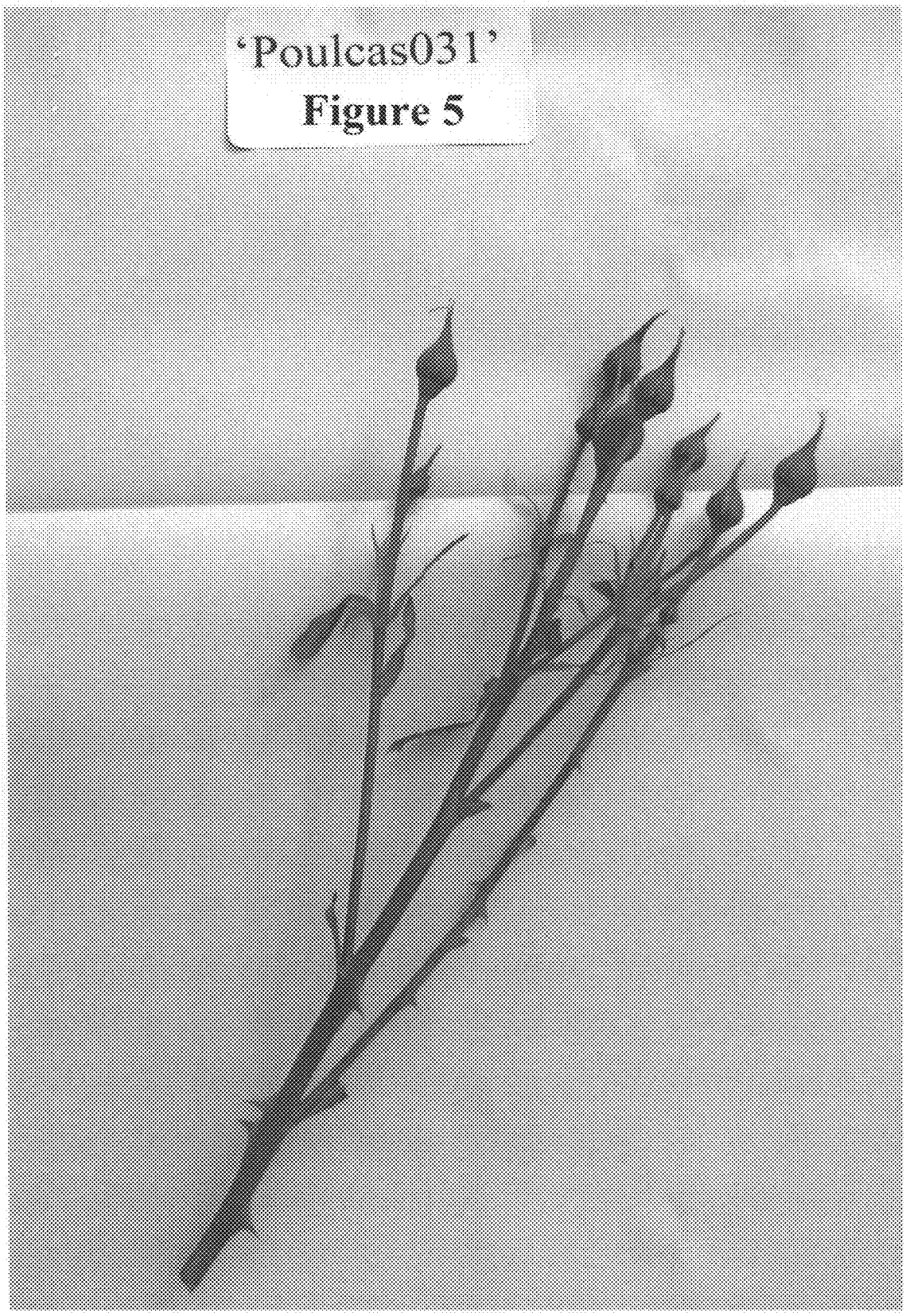
FIG. 5; Bare flowering branch with flower buds.

The following is a description of 'Poulcas031', as observed in its growth in in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulthe', U.S. Plant Pat. No. 10,879 are compared to 'Poulcas031' in Chart 1.

CHART 1

| | 'Poulcas031' | 'Poulthe' |
|---|---|---|
| Petal Count | 40 to 50 | 55 to 60 |
| Flower Diameter | 70 to 80 mm | 40 to 50 mm |
| General Tonality of Flower Color | Red-Purple Group N 57A | Red-Purple 57A |

FLOWER AND FLOWER BUD

Blooming habit: Continuous.

Flower bud:

*Size.*—Upon opening, 25 mm in length from base of receptacle to end of bud. Bud diameter is about 13 mm.

*Bud form.*—Urceolate.

*Bud color.*—As sepals unfold, petals are Red-Purple Group N57B.

*Sepal inner surface.*—Color: Yellow-Green Group 145 B. Surface: Moderate pubescence.

*Sepal outer surface.*—Color: Green Group 143C. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—25 to 30 mm long by 7 mm wide.

*Receptacle.*—Texture: Smooth. Shape: Campanulate. Size: 7 mm (height) and 7 mm (wide). Color: Green Group 143C.

*Peduncle.*—Length: 50 to 70 cm. Diameter: 3 to 4 mm. Color: Yellow-Green Group 146C.

*Pedicel.*—Surface: Some prickles. Length: 50 to 60 mm. Diameter: 2 to 3 mm. Color: Yellow-Green Group 146C. Strength: Strong.

Flower bud development: Flower buds are borne in clusters of 5 to 7 flower buds per stem.

Flower bloom:

*Fragrance.*—Medium floral scent.

*Duration.*—The blooms have a duration on the plant of approximately 8 to 10 days. Petals fall cleanly away from plant after flowers have fully matured.

*Size.*—Flower diameter is 70 to 80 mm when open. Flower depth is about 30 mm.

*Flower shape.*—General shape is a hybrid tea that opens quickly to become cup shaped with petals that curve out from the center. The reproductive parts remain hidden by the inner petals.

*Shape of flower, side view.*—Upon opening the upper portion is flat. The lower portion is flat. After opening, the upper portion is a flattened convex. The lower portion is flat.

Petalage: Under normal conditions, flowers have 40 to 50 petals total, 10 of which are petaloids.

Petal color:

*Upon opening, outer and inner petals.*—Upper surface: Red-Purple Group N57A. Lower surface: Red-Purple Group N57B to N57C.

*Basal petal spots, upon opening.*—Upper surface: Yellow Group 6C. Lower surface: Yellow Group 6D.

*After opening, outer and inner petals.*—Upper surface: Red-Purple Group N57A. Lower surface: Red-Purple Group N57B to N57C.

*Basal petal spots, after opening.*—Upper surface: Yellow Group 6C. Lower surface: Yellow Group 6D.

General tonality: On open flower Red-Purple Group N 57A. No change in the general tonality at the end of the 10th day.

Petals:

*Petal reflex.*—Flat.

*Margin.*—Entire and uniform.

*Shape.*—Generally narrow elliptic in shape. Apex shape: Rounded. Base shape: Acute.

*Size.*—40 to 30 mm (1)×40 to 25 mm (w).

*Texture.*—Smooth.

*Thickness.*—Average.

Petaloids:

*Quantity.*—10 on average.

*Shape.*—Asymmetric, with a rounded apex and an acute base point of attachment.

*Color.*—Upper surface is Red-Purple Group N57A. Lower surface is Red-Purple Group N57B to N57C. There are basal petal spots the color of upper surface Yellow Group 6C, and lower surface, Yellow Group 6D.

*Size.*—Approximately 15 mm long by 15 mm wide.

Reproductive organs:

*Pollen.*—None observed.

*Anthers.*—Length: 2 mm. Color: Yellow Group 13C. Quantity: 75 on average.

*Filaments.*—Color: Yellow Group 12 A. Length: 5 mm.

*Pistils.*—Length: 7 mm. Quantity: 50 on average.

*Stigmas.*—Superior to the anthers. Color: Yellow Group 4D.

*Styles.*—Color: Green-White Group 157A.

*Hips.*—None Observed in the field nursery in Jackson County Oreg.

PLANT

Plant growth: Upright to bushy. When grown as a budded field grown plant on *Rosa multiflora* understock, the average height of the plant is 90 cm and the average width is 90 cm.

Stems:

*Color.*—Juvenile growth: Yellow Green Group 144A. Mature growth: Green Group 138A.

*Length.*—On average, canes are 50 cm from the base of the plant to the flowering portion.

*Diameter.*—5 mm average.

*Surface texture.*—Young wood: Smooth. Older wood: Smooth.

Prickles:

*Incidence.*—7 prickles per 10 cm of stem.

*Size.*—Average length of prickles on mature stems is 6 mm.

*Shape.*—Deeply concave underneath the linear upper side.

*Color.*—Juvenile prickles: Yellow-Green Group 144C with some having intonations of Greyed-Red Group 180C. Mature prickles: Yellow-Green Group 144C.

Plant foliage: Normal number of leaflets leaves in middle of the stem: 7 leaflets.

*Compound leaf.*—120 mm (1)×75 (w).

*Quantity.*—3 leaves per 10 cm of stem on average.

*Color of mature foliage.*—Upper side: Yellow-Green Group 147A. Lower side: Yellow-Green Group 147C.

*Color of juvenile foliage.*—Upper side: Yellow-Green Group 146B with intonations of Greyed-Red Group 178A. Lower side: Yellow-Green Group 146C.

Plant leaves and leaflets:

*Stipules.*—Size: 20 to 30 mm in length. Quantity: 2 per compound leaf. Shape: Linear, slightly broad based with outward extending apices. Margins: Finely serrated with few stipitate glands. Color: Yellow-Green Group 144B.

*Petiole.*—Length: 30 mm. Diameter: 2 mm.

*Upper petiole surface.*—Color: Yellow-Green Group 144A. Observations: Stipitate glands.

*Lower petiole surface.*—Color: Yellow-Green Group 144B.

*Rachis.*—Length: 50 to 75 mm.

*Upper rachis surface.*—Color: Yellow-Green Group 144A. Observations: Stipitate glands.

*Lower rachis surface.*—Color: Yellow-Green Group 144B.

*Leaflet.*—Edge: Serrated. Size: Average size of the terminal leaflet on normal leaves is 55 mm in length by 40 mm wide. Shape: Obovate. Base: Rounded. Apex: Cuspidate. Texture: Smooth. Thickness: Average. Arrangement: Odd pinnate. Venation: Reticulate. Glossiness: Very Glossy.

Disease resistance: Above average resistance to powdery and downy mildew, rust, black spot, and Botrytis under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the compact floribunda rose class named 'Poulcas031', substantially as illustrated and described herein, due to its abundant pink flowers, disease resistance, and extended period of bloom.

* * * * *

'Poulcas031'

'Poulcas031'

'Poulcas031'

'Poulcas031'